United States Patent [19]

Gansow et al.

[11] Patent Number: 5,434,287

[45] Date of Patent: * Jul. 18, 1995

[54] BIFUNCTIONAL DTPA-TYPE LIGAND

[75] Inventors: Otto A. Gansow, Washington, D.C.; Martin W. Brechbiel, Annandale, Va.

[73] Assignee: The United States of America as represented by the Department of Health and Human Services, Washington, D.C.

[*] Notice: The portion of the term of this patent subsequent to Jun. 23, 2009 has been disclaimed.

[21] Appl. No.: 147,957

[22] Filed: Nov. 4, 1993

Related U.S. Application Data

[62] Division of Ser. No. 881,049, May 11, 1992, Pat. No. 5,286,850, which is a division of Ser. No. 498,319, Mar. 16, 1990, Pat. No. 5,124,471.

[51] Int. Cl.$^6$ ............... C07C 331/28; C07C 205/06; C07C 211/44; C07C 211/65

[52] U.S. Cl. ...................... 558/17; 562/434; 562/435; 562/443; 562/450

[58] Field of Search ............... 562/434, 443, 450, 435; 558/17

[56] References Cited

U.S. PATENT DOCUMENTS

| | | |
|---|---|---|
| 4,339,426 | 7/1982 | Meares et al. |
| 4,454,106 | 6/1984 | Gansow et al. |
| 4,472,509 | 9/1984 | Gansow et al. |
| 4,824,986 | 4/1989 | Gansow . |
| 4,831,175 | 5/1989 | Gansow et al. |
| 4,849,505 | 7/1989 | Stavrianopoulos . |
| 4,881,175 | 11/1989 | Ladner . |

FOREIGN PATENT DOCUMENTS

| | | |
|---|---|---|
| 713093 | 7/1965 | Canada . |
| 0279307 | 8/1988 | European Pat. Off. |
| 1155122 | 10/1963 | Germany . |
| WO86/06605 | 11/1986 | WIPO . |

OTHER PUBLICATIONS

Huneke et al., "Effective α-Particle-mediated Radioimmunotherapy of Murine Leukemia," *Cancer Res.*, 52, 5818-5820 (1992).

McCall et al., "Simplified Method for Conjugating Macrocyclic Bifunctional Chelating Agents to Antibodies via 2-Iminothiolane," *Bioconjugate Chem.*, 1(3), 222-226 (1990).

Mirzadeh et al., "Radiometal Labeling of Immunoproteins: Covalent Linkage of 2-(4-Isothiocyanatobenzyl)-diethylenetriaminepentaacetic Acid Ligands to Immunoglobulin," *Bioconjugate Chem.*, 1(1), 59-65 (1990).

Rodwell et al., "Site-specific Covalent Modification of Monoclonal Antibodies: In vitro and in vivo Evaluations," *Proc. Natl. Acad. Sci. USA*, 83, 2632-2636 (1986).

Waldmann, "Monoclonal Antibodies in Diagnosis and Therapy," *Science*, 252, 1657-1662 (1991).

Brechbiel et al., "Synthesis of 1-(p-Isothiocyanatobenzyl) Derivatives of DTPA and EDTA. Antibody Labeling and Tumor-Imaging Studies," *Inorganic Chemistry*, 25: 2772-2781, Jul. 30, 1986.

Gansow et al., "Generator-Produced Bi-212 Chelated to Chemically Modified Monoclonal Antibody for Use in Radiotherapy," *ACS Symposium Series 241*, Chapter 15, Radionuclide Generators, 215-227. 1984.

Hnatowich et al., "DTPA-Coupled Antibodies Labeled wtih Yttrium-90," *J. Nucl. Med.*, 26(5): 503-509. May 1985.

Hnatowich et al., "The Preparation and Labeling of DTPA-Coupled Albumin," *Int. J. Appl. Radiat. Isot.*, 33: 327-332. 1982.

Khaw et al., "Myocardial Infarct Imaging of Antibodies to Canine Cardiac Myosin with Indium-111-Diethylenetriamine Pentaacetic Acid," *Science*, 209: 295-297. Jul. 1980.

(List continued on next page.)

*Primary Examiner*—Johann Richter
*Assistant Examiner*—John Peabody
*Attorney, Agent, or Firm*—Leydig, Voit & Mayer, Ltd.

[57] ABSTRACT

The subject matter of the present invention relates to bifunctional cyclohexyl DPTA ligands and methods for utilizing these compounds.

20 Claims, 1 Drawing Sheet

OTHER PUBLICATIONS

Kozak et al., "Bismuth-212-labeled anti-Tac monoclonal antibody: α-Particle-emitting radionuclides as modalities for radioimmunotherapy," Proc. Natl. Aad. Sci. USA, 83: 474-478. Jan. 1986.

Kozak et al., "Nature of the Bifunctional Chelating Agent Used for Radioimmunotherapy with Yttrium-90 Monoclonal Antibodies: Critical Factors in Determining in Vivo Survival and Organ Toxicity," Cancer Research, 49: 2639-2644. May 15, 1989.

Kozak et al., "Radionculide-conjugated monoclonal antibodies: a synthesis of immunology, inorganic chemistry and nuclear science," Tibtech, 259-263. Oct. 1986.

Krejcarek et al., "Covalent Attachment of Chelating Groups to Macromolecules," Biochemical and Biophysical Research Communications, 77(2): 581-585. 1977.

Macklis et al., "Radioimmunotherapy with Alpha-Particle-Emtiting Immunoconjugates," Science, 240: 1024-1026. 1988.

Magerstädt et al., "Gd(DOTA): An Alternative to Gd(DTPA) as a $T_{1,2}$ Relaxation Agent for NMR Imaging or Spectroscopy," Magnetic Resonance in Medicine, 3: 808-812. 1986.

Meares et al., "Conjugation of Antibodies with Bifunctional Chelating Agents: Isothiocyanate and Bromoacetamide Reagents, Methods of Analysis, and Subsequent Addition of Metal Ions," Analytical Biochemistry, 142: 68-78. 1984.

Morrison, "Genetically Engineered (Chimeric) Antibodies," Hospital Practice, 65-80. Oct. 15, 1989.

Paik et al., "Reduction of Background Activities by Introduction of a Diester Linkage Between Antibody and a Chelate in Radioimmunodetection of Tumor," J. Nucl. Med., 30(10): 1693-1701. Oct. 1989.

Rainsbury et al., "Tumor Localization With Monoclonal Antibody Radioactively Labelled with Metal Chelate Rather Than Iodine," The Lancet, 1347-1348. Dec. 11, 1982.

Scheinberg et al., "Tumor Imaging with Radioactive Metal Chelates Conjugated to Monoclonal Antibodies," Science, 215: 1511-1513. Mar. 19, 1982.

Spirlet et al., "Structural Characterization of a Terbium(III) Complex with 1,4,8,11-Tetraazacyclotetradecane-1,4,8,11-tetraacetic Acid. Lanthanide Ions and the Conformation of the 14-Membered Macrocycles," Inorg. Chem., 23: 4278-4283. 1984.

BIFUNCTIONAL DTPA-TYPE LIGAND

This is a continuation of copending application Ser. No.07/881,049, filed May 11, 1992, now U.S. Pat. No. 5,286,850, which is, in turn a divisional of Ser. No. 07/498,319filed Mar. 26, 1990, now U.S. Pat. No. 5,124,471.

BACKGROUND OF THE INVENTION

1. Technical Field

The subject matter of the present invention relates to bifunctional cyclohexyl DTPA ligands and methods of using these compounds. Specifically, such ligands are useful for radiolabeling proteins with radioactive metals, and can consequently be utilized with respect to radioimmunoimaging and/or radioimmmunotherapy.

2. Background Information

This invention relates to metal chelates and the use of metal-chelate protein conjugates.

Interest in the art of metal chelates and in methods for forming metal chelate-protein conjugates for diagnostic and therapeutic purposes continues. Representative type chelates and conjugates and methods for forming conjugates are disclosed, inter alia, in U.S. Pat. Nos. 4,454,106, 4,472,509, 4,339,426, in EPA O 279 307 and in German Patent 1,155,122. Other proteins including antibodies, monoclonal antibodies and fragments thereof, monoclonal antibodies and fragments thereof which have been structurally altered by recombinant DNA techniques (i.e., chimeric antibodies), polyclonal antibodies, antigens, blood proteins, or proteins bound to blood lymphocytes or other cells can also be employed in the formation of conjugates.

A method for synthesis of bifunctional metal chelates for conjugation to proteins involves reduction of amino acid amides to ethylenedismines to form monosubstituted derivatives which are converted to bifunctional ethylenediaminetetraacetic acid (EDTA) chelates by alkylation with haloacetic acid. (Yeh et al., *Anal. Biochem.* 100:152 (1979)). Similarly, a monosubstituted diethylenetriamine is synthesized by reaction of ethylenediamine with an amino acid ester and reduction of the resulting amide carbonyl. (Brechbiel et al. *Inorg. Chem.* 25: 2772-2781 (1986)). Alkylation of the diethylenetriamine with haloacetic acid produces a monosubstituted bifunctional diethylenetriaminepentaacetic acid (DTPA) chelate.

Another method of synthesis of a bifunctional DTPA involves reaction of a DTPA or EDTA carboxylate with a chloroformate ester to form a reactive anhydride. (Krejcarek et al., *Biochem. Biophys Res. Commun.* 77(2):581-585 (1977)). The dianhydride of DTPA used as a bifunctional chelate is prepared by dehydration of the parent DTPA. (Hnatowich et al., *Int. J. Appl. Rad. Isot.* 33:327-332 (1982)). The practice of using an EDTA chelate monosubstituted at the carbon-1 position to better retard the release of metal from chelate in vitro, than the unsubstituted EDTA chelate, has also been reported. (Meares et al., *Anal. Biochem.* 142:68-78 (1984)).

The prior art has formed metal-protein chelate conjugates by mixing monosubstituted bifunctional EDTA or DTPA chelates or DTPA anhydrides with proteins followed by reaction with the metal to be chelated. (Krejcarek et al., *Biochem. Biophys. Res. Commun.* 77(2):581-585 (1977); Brechbiel et al., *Inorg. Chem.* 25:5783 (1986)). Imaging of tumor target sites in vivo with metal chelate conjugated monoclonal antibodies prepared according to these methods has been reported. (Khaw et al., *Science* 209:295-297 (1980); Sheinberg et al., *Science* 215:1511-1513 (1982)), Diagnosis of human cancer in vivo using metal chelate conjugated monoclonal antibody has also been reported. (Rainsbury et al., *Lancet,* 1347-1348 (1982)). The use of chimeric antibodies and advantages thereof have been discussed by Morrison, S. L., *Hospital Practice* (Office Edition) 68-80 (1989). The potential efficacy of using a linking group within a chelate conjugated protein has also been discussed (Paik et al,, *J. Nucl. Med.* 30(10):1693-1701 (1989)).

However, attempts to employ the tumor localizing properties of metal chelate conjugated monoclonal antibodies for therapeutic purposes have not found common usage, in part because metals may be (and often are) released from the metal chelate conjugate in vivo and, particularly in the case of radioactive metal salts, may produce undesirable concentrations of toxic radionucleotides in bone marrow or kidney or the like even if the conjugates are rigorously purged of adventitiously bonded metal. A process for purifying metal chelate protein conjugates of adventitiously bonded metals is disclosed in U.S. Pat. No. 4,472,509. The importance of using very strong metal chelates to firmly link radiometals to monoclonal antibodies and of rigorous purification of the conjugates to effect maximal tumor localization and minimize delivery to non-target tissues is discussed in Brechbiel et al., *Inorg. Chem.* 25:2772-2787 (1986)) . Undesirable localization of potentially therapeutic radionuclides released in mice in vivo from metal chelate conjugated polyclonal antibodies have precluded some therapy investigations in humans. (Vaughn et al., *EIR-Bericht.* Vol. 78, (1986)). Increased in vivo bone uptake of radiometal injected for therapy as a metal chelate conjugated monoclonal antibody has also been reported. (Hnatowich et al., *J. Nucl. Med.* 26(5):503-509 (1985)). The amount of potentially therapeutic doses in humans of radiometal chelated polyclonal antibody has been limited by bone marrow toxicity (Order et al., *Int. J. Rad. Oncol.* 12:277 (1986)). Kidney uptake of radiometal has recently been reported as preventing human use. (Macklis et al, *Science,* 240:1024-1026 (1988) ).

Disubstituted bifunctional DTPA derivatives have proven useful for labeling of proteins with radioactive metals (Kozak, et al., *Cancer Research* 49:2639-2644 (1989) ). The introduction of a second substituent on the carbon backbone of DTPA was seen to retard the loss of metal from the DTPA ligand when linked to antibody and injected into the circulation of animals.

The usefulness of radionuclide materials in cancer therapy is disclosed in the article, Kozak et al., "Radionuclide-conjugated monoclonal antibodies: A Synthesis of Immunology, Inorganic Chemistry and Nuclear Science" *Tends in Biotechnology,* 4(10):259-264 (1986). This article discusses the use of antibody conjugates to deliver either alpha or beta radiation. The value of alpha radiation for bismuth-212 in radionuclide therapy is further discussed in the two articles, Kozak et al., "Bismuth-212-labeled anti-Tac monoclonal antibody: Alpha-particle-emitting Radionuclides as Modalities for Radiommunotherapy, " *Proc. Natl. Acd. Sci. U.S.A.* 83:474-478 (1986) and Gansow et al., "Generator-produced Bi-212 Chelated to Chemically Modified Monoclonal Antibody for Use in Radiotherapy," *Am. Chem. So. Symposium Series* 241, chapter 15, 215–227 (1984). Ligands, for the secure linkage of bismuth to proteins, have not been available. (Macklis et al., *Science* 240:1024–1026 (1988)).

Examples of other uses for chelated metal ions are disclosed in the following articles. Magerstadt et al., "Gd (DOTA): An alternative to Gd (DPTA) as a T$\frac{1}{2}$ Relaxation Agent for NMR Imaging or Spectroscopy," *Magnetic Resonance in Medicine* 3:808–812 (1986), discloses the usefulness of gadolinium as a relaxation agent for NMR imaging. The article, Spirlet et al., "Structural Characterization of a Terbium (III) Complex with 1,4,8,11-Tetraazacyclotetradecane-1,4,8,11 tetraacetic acid. Lanthanide Ions and the Conformation of the 14- Membered Macrocycles," *Inorgan. Chem.* 23:4278–4283 (1984), disclosed the usefulness of lanthanide chelates.

All patents and publications referred to herein are hereby incorporated by reference.

It is evident from the above that there continues to be a need for more effective metal chelate protein conjugates that firmly link metals to proteins to minimize metal release and permit highly selective delivery of metals to targeted sites in vivo.

SUMMARY OF THE INVENTION

It is, therefore, an object of the present invention to provide novel polysubstituted cyclohexyl diethylenetriamines.

It is another object of the present invention to provide novel polysubstituted bifunctional cyclohexyl diethylenetriaminepentaacetic acid ligands or chelates.

It is yet another object of this invention to provide novel ligand and chelate-hapten conjugates.

It is still further object of this invention to provide novel metal chelate protein conjugates.

It should be noted that the present invention overcomes an inherent synthetic barrier which limits the prior art to less than three ligand substitutents without stereo-control.

The present invention includes a ligand comprising: a general Formula I:

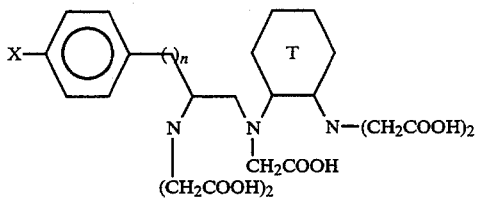

wherein n is an integer from 1 to 5;
X equals —NO$_2$, —NH$_2$, —NCS, or —NHCOCH$_2$—Z;
T denotes the trans isomer of the cyclohexyldiamine substructure; and
Z is chloride, bromide or iodide.

The invention also includes a metal chelate of the ligand wherein n is an integer from 1 to 5, X equals —NO$_2$, —NH$_2$, —NCS, or —NHCOCH$_2$—Z, the metal is chosen from the elements consisting of Cu, Pb, In, Yt, Bi, the lanthanides, Au, Ag, and Ga, and Z is is chloride, bromide or iodide.

In addition, the invention includes a ligand-hapten conjugate comprising:
the general Formula II:

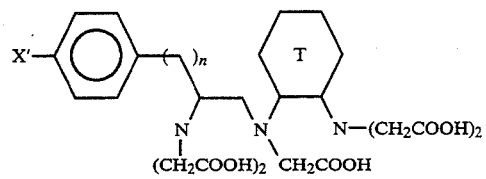

wherein n is an integer from 1 to 5;
X' is NH—Q, NHCS—Q or —NHCOCH$_2$ where Q is a hapten chosen from the group consisting of steroids, enzymes, proteins, monoclonal antibodies, chimeric antibodies, or fragments thereof; and
T denotes the trans isomer of the cyclohexyldiamine substructure.

Another embodiment of the invention includes the ligand-hapten conjugate wherein n is an integer from 1 to 5, X' is equal to —NH—L—Q, —NHCS—L—Q, or —NHCOCH$_2$—L—Q, where Q is a hapten selected from the group consisting of steroids, enzymes, proteins, monoclonal antibodies, chimeric antibodies, or fragments thereof, and L is a covalent linking group.

A further embodiment includes the situation where L of the ligand-hapten conjugate is selected from the group consisting of an organic radical, or a substituted aliphatic hydrocarbon chain. The chain may be interrupted by one or more hetero atoms selected from —O— or —S—, or one or more —NR'— groups, where R' is a hydrogen atom or a alkyl group, —CONR'— groups, —NR'CO— groups, cycloaliphatic, aromatic or heteroaromatic groups, or a mixture thereof.

A further embodiment includes the metal chelates of the ligand-hapten conjugate wherein n is an integer from 1 to 5, X' is equal to —NH—Q, —NHCS—Q or —NHCOCH$_2$—Q where Q is a hapten selected from the group consisting of steroids, enzymes, proteins, monoclonal antibodies, chimeric antibodies, or fragments thereof, and the metal is selected from the group consisting of Cu, Pb, In, Y, Bi, the lanthanides, Au, Ag, and Ga.

An additional embodiment includes the metal chelates of the ligand-hapten conjugate wherein n is an integer from 1 to 5, X' is equal to —NH—L—Q, —NHCS—L—Q or —NHCOCH$_2$—L—Q where Q is a hapten selected from the group consisting of steroids, enzymes, proteins, monoclonal antibodies, chimeric antibodies, or fragments thereof, the metal is selected from the group consisting of Cu, Pb, In, Y, Bi, the lanthanides, Au, Ag, and Ga, and L is a covalent linking group.

Another embodiment includes the situation where L of the metal chelates of the conjugate is selected from the group consisting of an organic radical or a substituted aliphatic hydrocarbon chain. The chain may be interrupted by one or more hetero atoms selected from —O— or —S— or by one or more —NR'— groups, where R' is a hydrogen atom or a $c_{-1}$ alkyl group, —CONR'— groups, —NCR'O— groups, cycloaliphatic groups, aromatic or heteroaromatic groups, or a mixture thereof.

The present invention also includes the method of using the metal chelates of the ligand-hapten conjugate wherein said conjugate is administered to a patient as a therapeutic agent or diagnostic agent.

Furthermore, the present invention includes the method of using the metal chelates of the ligand-hapten conjugate possessing a linking group wherein the chelate as a therapeutic or diagnostic agent.

DETAILED DESCRIPTION OF INVENTION

Figure 1:
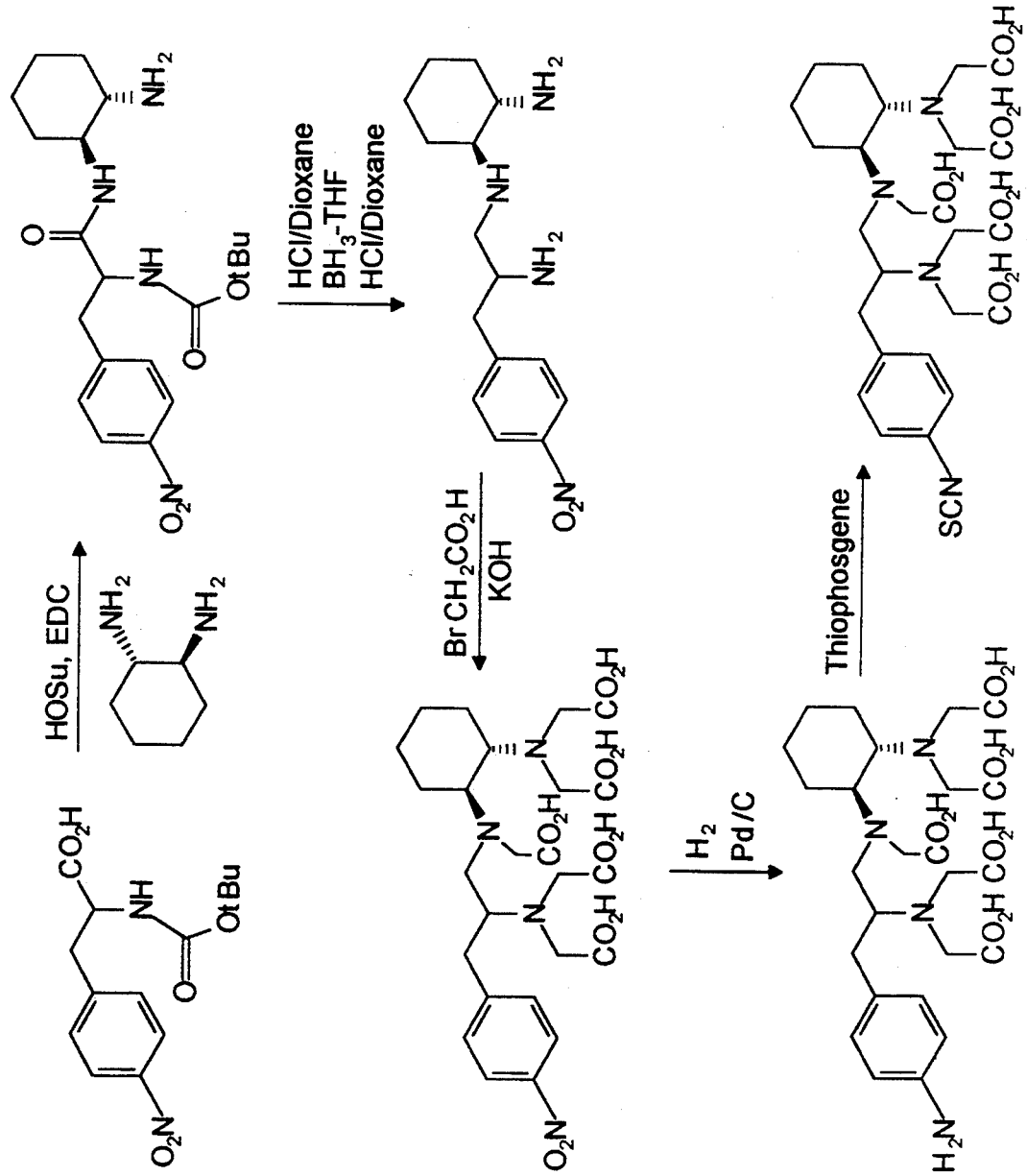
FIG. 1 represents a scheme for the preparation of a substituted cyclohexyl diethylenetriaminepentaacetic acid ligand (DTPA).

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The subject matter of the present invention relates to bifunctional cyclohexyl DTPA chelating agents or ligands and methods for using these compounds. Specifically, the ligands can be used in radioimmunoimaging and/or radioimmunotherapy, as the compounds may be utilized for labeling proteins with radioactive metals.

Monoclonal antibodies are immunoglobulins of well-defined chemical structure, in contrast to polyclonal antibodies which are heterogeneous mixtures of immunoglobulins. A characteristic feature of monoclonal antibodies is reproducibility of function and specificity, and such antibodies can be and have been developed for a wide variety of target antigens, including tumor cells. More recently, chimeric monoclonal antibodies and fragments have been prepared by recombinant techniques (Morrison, S. L., *Hospital Practice (Office Edition)*, 65–80, 72–74, 77–80 (1989)).

Methods for obtaining monoclonal antibodies or fragments have been extensively discussed and are well-known in the art. A useful text is *Monoclonal Antibodies* (R. H. Kennett, T. J. McKearn & K. B. Bechtol eds. 1980). See also Koprowski et al. (U.S. Pat. No. 4,196,265). The selections of a monoclonal antibody for the practice of this invention will depend upon the end use for which the metal chelate conjugated monoclonal antibody will be employed. Such selection is within the skill of the art.

A wide variety of organic chelating agents or ligands can be conjugated to monoclonal antibodies. Organic ligands to be conjugated to monoclonal antibodies may be chosen from among either the natural or synthetic amines, porphyrins, aminocarboxylic acids, iminocarboxylic acids, ethers, thiols, phenols, glycols and alcohols or the polyamines, polyaminocarboxylic acids, polyiminocarboxylic acids, aminopolycarboxylic acids, iminopolycarboxylic acids, nitrilocarboxylic acids, dinitrilopolycarboxlic acid, polynitrilopolycarboxylic acids, ethylunediaminetetracetates, diethylenetriaminepenta or tetraacetates, polyethers, polythiols, cryptands, polyetherphenolates, polyetherthiols, ethers of thioglycols or alcohols, polyaminephenols, all either acyclic, macrocyclic, cyclic, macrobicyclic or polycyclic, or other similar ligands which produce highly stable metal chelates or cryprates.

The ligand of this invention possesses a nonmetal bonded organic functional group suitable for bonding to the monoclonal antibody. Functional groups may be chosen from among the carboxylic acid groups, diazotiazable amine groups, N-hydroxysuccinimidyl, esters, anhydrides, mixed anhydrides, maleimides, hydrazines, benzimidates, nitrenes, isothiocyanates, azides, sulfonamides, bromoacetamides, iodocetamides, carbodiimides, sulfonylchlorides, hydroxides, thioglyols, or any reactive functional group known in the art as a biomolecular conjugating or coupling agent.

The present invention is a derivative of diethylenetriaminepentaacetic acid (DTPA). It has been found that DTPA ligands tightly bind metal ions and that the DTPA derivative of this invention forms a chelate conjugated monoclonal antibody that is highly stable, both with respect to the metal chelate binding and with respect to chelate-antibody conjugate. These properties are of great importance, particularly for in vivo applications. For example, if the chelate releases the metal ion after introduction into the blood, these ions tend to be bound by transferrin, or the like, and be distributed generally in the circulatory system of the body. Moreover, the ions will ultimately tend to collect and remain in organs such as the liver and spleen, bone or kidney. These effects can have serious consequences depending on the toxicity of the metal and its radioactivity. Furthermore, if the chelate does not form a highly stable conjugate with the antibody, there is a significant reduction in the amount of metal delivered to the target site and a corresponding decrease in efficacy. If the conjugate is used for diagnostic purposes, release of the metal can undesirably increase background radiation.

The metals which may be employed in the present invention may include radioactive or nonradioactive elements with a valance of two or higher. Monovalent metals generally do not form sufficiently stable chelates for the purposes of this invention. Representative radioactive elements may include d-block transition metals, the group IIIA, IVA, VA metals, the lanthanides or the actimides. Nonradioactive metals may be selected, for example, for their useful physical properties such as paramagnetism, fluorescence, or phosphorescence. Representative nonradioactive metals include most lanthanides and some first row d-block elements. While this invention is discussed in terms of metals or metal chelates, it will be understood that metal ions are, in fact, chelated in the conjugate.

If the metal chelate conjugated monoclonal antibody to be used for imaging in vivo, a gamma or positron emitting radiometal, such as indium-111 (gamma) or gallium-68 (positron), can be used depending upon the chosen method of detection. For purposes of therapy, the radiometals may be alpha (e.g. bismuth-212), beta (e.g. Pb-212, Y-90 or Cu-67 scandium-47) or Auger electron emitter. An alpha emitter, such as bismuth-212 is desirably employed for therapy. Paramagnetism, fluorescence and phosphorescence can be used, for example, for in vitro tests. The choice of any particular metal and valence state is within the skill of the art.

Metal chelation is carried out in an solution and, desirably avoids the use of strong acids or bases. Metal chelation for any chelate-antibody conjugate is carried out at a pH which does not significantly reduce the biological activity or specificity of the antibody. Generally, the acceptable range is from about pH 3.2 to about pH 9, however, particular antibodies may have to be restricted to a narrower range. At a pH above 3.5, adventitious binding of metal ions to antibodies is substantially impaired for many metals. A preferred range, therefore, is often from about pH 3.2 to about pH 3.5. Factors peculiar to solutions of the metal employed, however, may permit a pH abut 3.5. The selection of the appropriate pH within the range is within the skill of the art.

Linkage of bismuth ions to antibodies by use of metal chelates is a particularly difficult process. Only the iodide complexes label ligand linked antibodies effectively (Kozak et al., *Proc. Nat. Acad. Sci* 83:474–478 (1986)). Moreover, no chelating agents are currently available which bind bismuth securely in vivo (Macklis et al., *Science*, 240:1024–1026 (1988)).

The functionalized DTPA ligand of the present invention is substituted on three carbon positions as is drawn in Formula I (shown below) in which X represents the nitro, amino, isothiocyanate or haloacetimide functional groups, n=1 to 5, and the symbol T in the cyclohexane ring denotes the trans isomer of the diaminecyclohexyl substructure.

The structure of Formula I is as follows:

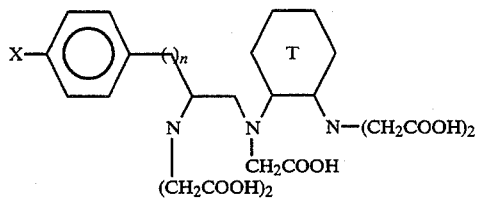

The invention also includes the metal chelates of the ligand of Formula I. Herein, the metals are chosen from the elements including copper, lead, indium, yttrium, bisbuth, the lanthanides, gold, silver, and gallium.

Particularly preferred embodiments of the invention involve metal chelates of the ligand of Formula I with the radioactive isotopes In-111, Y-90, Bi-212, Pb-202, Pb-212, Ga-66, Ga-67, Ga-68, and Cu-67.

The presence of three substituents on the carbon backbone of DTPA induces a maximal control of the stereochemical predisposition of the ligand towards effective metal complexation. In particular, the introduction of the trans structure of the cyclohexyldiamine substructure of Formula I is well known to increase metal complex thermodynamic stability as opposed to the similar cis cyclohexyldiamine isomer as evidenced for the well characterized cis and trans cyclohexyl-EDTA complexes. See data in A. E. Martell, *Critical Stability Constants*, Vol. 1, Plenum Press, New York, (1974). Additionally, the stereochemical constraint of the cyclohexane ring serves to direct and focus the lone pairs of the two amines to impart maximal overlap with available empty metal orbitals, and as well as to maximize ligand-dipole to metal electostatic bonding. This results in a DTPA ligand with optimized pre-control and pre-organization for metal ion binding thus reducing the entropy of metal complex formation as recorded in the reference above.

Other functionalized DTPA ligands which feature trisubtitution on the carbon backbone have been envisioned, but they lack the critical stereochemistry of the trans cyclohexyldiamine substructure of Formula I. See U.S. Patent No. 4,831,175.

A principal advantage of the ligand of Formula I is that it forms complexes with bismuth ions that are stable in vivo. Such complexes of other substituted DTPA ligands are not stable in vivo, thus precluding their use in cancer therapy when linked to antibodies.

An additional feature of the ligands of this invention is that they form stable complexes in vivo with a wide variety of other radiometals of use in cancer detection and therapy. Such metal ions include trivalent indium, yttrium, or scandium and divalent lead and copper. Indium-111 is often used for tumor imaging. Thus, a patient could be imaged with the In-111 antibody conjugate of the ligand of this invention and thereafter treated with the bismuth-212 complex of the same antibody chelate conjugate, thus facilitating calculation of the dose of radioactivity transported to the patients tumor and so increasing likelihood of the effective application of the therapy. With dosimetry information, multiple dosing therapies can be designed.

Another embodiment of the invention is a ligand-hapten conjugate as is drawn in Formula II (shown below) in which the T in the cyclohexane ring denotes the trans isomer of the cyclohexyldiamine substructure, n is 1 to 5, and X' is —NH—Q, —NHCOCH$_2$-Q or NHCS—Q where Q is a hapten chosen from the group consisting of steroids, enzymes, or proteins. Of particular interest within the subset of proteins are monoclonal antibodies, chimeric monoclonal antibodies, and the fragments thereof.

The structure of Formula II is as follows:

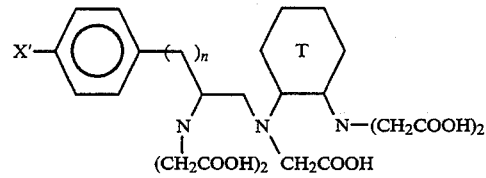

A further embodiment of the invention is a ligand-hapten conjugate as is drawn Formula II (shown above) in which the T in the cyclohexane ring denotes the trans isomer of the diamino cyclohexane substructure, n is 1 to 5, X' is —NH—L—Q, or —NHCS—L—Q where Q is a hapten chosen from the group consisting of steroids, enzymes, or proteins, and L is a covalent linking group. Of particular interest within the subset of proteins are monoclonal antibodies, chimeric monoclonal antibodies, and the fragments thereof. Such conjugates may be utilized as therapeutic and diagnostic agents.

The nature of the L group as a linker group is such that it may be varied widely without affecting the usefulness of the compounds of Formula I and Formula II, and the metal complexes thereof. Thus, L may be any suitable organic radical and may be, for instance, an optionally substituted aliphatic hydrocarbon chain, optionally interrupted by one or more hetero atoms selected from —O— or —S— or by one or more —NR'— groups (where R' is a hydrogen atom or a alkyl group), —CONR'— groups, —NR'CO— groups, cycloaliphatic groups, aromatic groups, heteroaromatic groups, or a mixture thereof.

Yet another embodiment of the present invention includes the metal chelates of the conjugate of Formula II. Herein, the metals are chosen from the elements including copper, lead, indium, yttrium, bismuth, the lanthanides, gold, silver, and gallium. Such metal chelates may also be utilized as therapeutic and diagnostic agents.

Particularly preferred embodiments of the present invention involve metal chelates of the ligand of Formula II with the radioactive isotopes. In-111, Y-90, Bi-212, Pb-202, Pb-212, Ga-66, Ga-67, Ga-68, and Cu-67.

The metal chelate conjugated antibodies of this invention can be administered in vivo in any suitable pharmaceutical carrier. As noted earlier, a physiologic normal saline solution can appropriately be employed. Often the carrier will include a minor amount of carrier protein such as human serum albumin to stabilize the antibody. The concentration of metal chelate conjugated antibodies within the solution will be e matter of choice. Levels of 0.5 mg per ml are readily attainable but the concentrations may vary considerably depending upon the specifics of any given application. Appropriate concentrations of biologically active materials in a carrier are routinely determined in the art.

The effective dose of radiation or metal content to be utilized for any application will also depend upon the particulars of that application. In treating tumors, for example, the dose will depend, inter alia, upon tumor burden, accessibility and the like. Somewhat similarly, the use of metal chelate conjugated antibodies for diagnostic purposes will depend, inter alia, upon the sensing apparatus employed, the location of the site to be examined and the like. In the event that the patient has circulating antigen in addition to those located at the site, the circulating antigens can be removed prior to treatment. Such removal of antigens can be accomplished, for example, by the use of unlabeled antibodies, or by plasmaphoresis in which the patient's serum is treated to removed antigens.

The invention is better illustrated by the following non-limiting examples, all of which relate to the synthesis represented in FIG. 1.

EXAMPLE 1

Preparation of BOC-p-nitro phenylalaine transcyclohexldiamine monoamide

The typical procedure used to prepare the active ester was to dissolve the BOC acid, N-hydroxysuccinamide, and EDC (48 mmol) in ethyl acetate ((400 mL). The mixture was stirred for 12 hours. The reaction solution was then filtered, and the filtrate was washed sequentially with saturated salt solution, 1M HCl, 5% $NaHCO_3$, and saturated salt solution (200 mL each). The organic layer was separated and dried over $MgSO_4$. After filtering, the solution was rotary evaporated to a solid. The solid was taken up in DMF (200 mL) and added dropwise to trans-1,2-diaminocyclohexane over a period of 18 hours. The precipitated diamide was filtered off, and the solution was rotary evaporated to a thick oil. The residue was taken up in chloroform and washed, as above, to remove any of the starting materials. The chloroform solution was dried as before, filtered, and concentrated to a gel-like consistency. This material was poured onto a Buchner funnel and triturated with petroleum ether to leave the product as a light tan solid.

EXAMPLE 2

Preparation of p-Nitrobenzyl-"CHX" diethylenetriamine

The BOC group was cleaved by stirring the amide (4.6 g) overnight in dioxane (300 mL) saturated with HCl. Addition of diethyl ether (200 mL), followed by cooling to 4° C., added significant precipitate. The dihydrochloride was collected on a Buchner funnel under argon and vacuum dried.

The amide dihydrochloride was suspended in THF (50 mL) in a three neck round bottom flask held in an ice bath. The flask was fitted with a condenser, thermometer, and a septum. Diborane/THF (6 eqv's) were injected into the flask, and the temperature was raised to 50° C. and maintained there until the reduction was complete. The progress of the reaction was monitored by HPLC using a ten minute gradient of 100% 0.1M HOAc in water to 100% 0.1M HOAc in methanol. The column was a Waters DeltaPak $C_{18}$.

After the reaction was finished, the solution was cooled to room temperature, and methanol (50 mL) was added to decompose any excess hydride. The solution was taken to dryness on the rotary evaporator, and the residue was taken up in 100% ethanol (100 mL). This solution was taken to dryness using a high vacuum rotary evaporator. Dioxane (150 mL), previously saturated with HCl, was added to the solid and the suspension as refluxed for four hours. The final suspension was left at 4° C. for 18 hours. The product was collected on a Buchner funnel under argon and then vacuum dried.

EXAMPLE 3

Preparation of p-Nitrobenzyl CHX DTPA

The triamine (1.0 g, 2.49 mmol) was dissolved in DMF (25 mL) with sodium carbonate (1.992 g), and tert-butyl bromoacetate (2.915 g, 14.95 mmol) was added. The solution was heated to about 80° C. overnight under argon after which the reaction mixture was poured into $H_2O$ (100 mL) and extracted with $CH_2Cl_2$ (100 mL). The organic layer was washed with water ($3 \times 100$ mL), separated, dried over $MgSO_4$, filtered, and rotary evaporated to an oil. The oil was further concentrated to a thick oil by high vacuum rotary evaporation. A CI-MS of this oil indicated that the penta ester was by far the principal product (greater than 70%).

The oil was treated with TFA (25 mL) overnight. The excess reagent was removed by rotary evaporation. HPLC revealed essentially two major peaks, 10.95 minutes and 11.9 minutes. The HPLC method was a gradient of 0.05M $Et_3N$/HOAc to 100% MeOH over 25 minutes. Preparative HPLC was performed to separate and collect the two peaks. After completion of the pre-HPLC, the HPLC buffer was removed by ion-exchange chromatography (AG50 W$\times$8 200/400 mesh H+ form). Analytical HPLC of the two separated fractions indicated two separated pure products. After lyophilization, the two fractions were each treated with bis(-trimethylsilyl) trifluoracetamide and EI-MS's were obtained. Each EI-MS gave the same M+ which in turn corresponded to the desired pentaacetic acid, each peak therefore being a separated pair of diastereomers now labeled a CHX-A or CHX-B.

EXAMPLE 4

Preparation of p-Aminobenzyl CHX DTPA-A, -B

Atmospheric hydrogenation of each fraction was performed using 100 mg of each nitro compound with 10% Pd/C (100 mg) at pH 8.5. The reaction was allowed to proceed until the $H_2$ uptake had halted. The reaction mixture was filtered on a fine frit with Celite 577. The filtrate was lyophilized to leave an off-white residue.

EXAMPLE 5

Preparation of p-Isothiocyanatobenzyl CHX DTPA-A, -B

Each fraction was dissolved in $H_2O$ (5 mL) and treated with thiophosgene (20 uL) in $CHCl_3$ (10 mL) with maximum stirring under argon for two hours. The organic layer was removed by room temperature rotary evaporation, and the aqueous layer was lyophilized to leave an off-white solid. I.R. spectrum of each fraction showed a good, strong band at 2100 cm$^{-1}$ for the aryl SCN group.

We claim:

1. A ligand of the formula

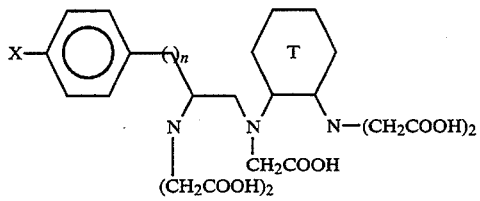

wherein n is an integer from 1 to 5; X is —NH$_2$, —NCS, or —NHCOCH$_2$—Z, where Z is chloride, bromide, or iodide; and T denotes the trans isomer of the cyclohexyldiamine substructure.

2. The ligand of claim 1, wherein X is —NH$_2$.
3. The ligand of claim 1, wherein X is —NCS.
4. The ligand of claim 1, wherein X is NHCOCH$_2$—Z.
5. The ligand of claim 4, wherein Z is chloride.
6. The ligand of claim 4, wherein Z is bromide.
7. The ligand of claim 4, wherein Z is iodide.
8. A metal chelate consisting of a ligand coordinated with a metal, wherein said ligand has the formula

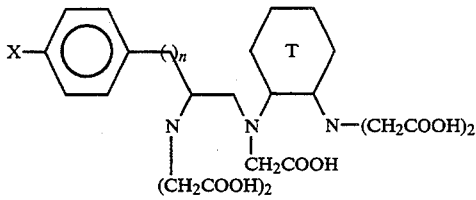

wherein n is an integer from 1 to 5; X is —NH$_2$, —NCS, or —NHCOCH$_2$—Z, where Z is chloride, bromide, or iodide; and T denotes the trans isomer of the cyclohexyldiamine substructure.

9. The metal chelate of claim 8, wherein said metal is selected from the group consisting of Cu, Pb, In, Y, Bi, the lanthanides, Au, Ag, and Ga.
10. The metal chelate of claim 9, wherein said metal is selected from the group consisting of radioisotopes.
11. The metal chelate of claim 10, wherein said metal is selected from the group consisting of α-particle emitting radioisotopes of bismuth.
12. The metal chelate of claim 11, wherein said metal is bismuth-212.
13. The metal chelate of claim 10, wherein said metal is selected from the group consisting of radioisotopes of bismuth.
14. A ligand of the formula

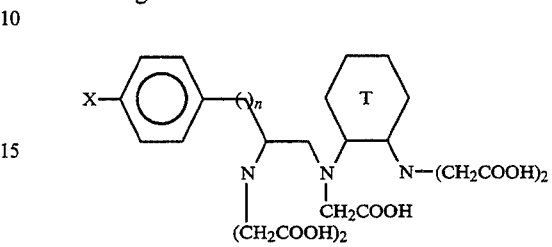

wherein n is an integer from 1 to 5; X is —NO$_2$; and T denotes the trans isomer of the cyclohexyldiamine substructure.

15. A metal chelate consisting of a ligand coordinated with a metal, wherein said ligand has the formula

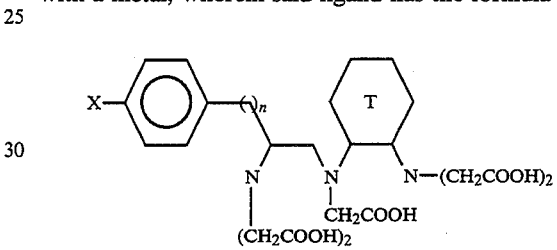

wherein n is an integer from 1 to 5; X is —NO$_2$; and T denotes the trans isomer of the cyclohexyldiamine substructure.

16. The metal chelate of claim 15, wherein said metal is selected from the group consisting of Cu, Pb, In, Y, Bi, the lanthanides, Au, Ag, and Ga.
17. The metal chelate of claim 16, wherein said metal is selected from the group consisting of radioisotopes.
18. The metal chelate of claim 17, wherein said metal is selected from the group consisting of α-particle emitting radioisotopes of bismuth.
19. The metal chelate of claim 18, wherein said metal is bismuth-212.
20. The metal chelate of claim 17, wherein said metal is selected from the group consisting of radioisotopes of bismuth.

* * * * *